United States Patent
Delache et al.

(10) Patent No.: US 7,448,383 B2
(45) Date of Patent: Nov. 11, 2008

(54) AIR ASSISTANCE APPARATUS PROVIDING FAST RISE AND FALL OF PRESSURE WITHIN ONE PATIENT'S BREATH

(75) Inventors: Alain Delache, Nice (FR); Véronique Delache, Nice (FR)

(73) Assignee: Kaerys, S.A., Nice (FR)

( * ) Notice: Subject to any disclaimer, the term of this patent is extended or adjusted under 35 U.S.C. 154(b) by 610 days.

(21) Appl. No.: 10/506,971

(22) PCT Filed: Mar. 10, 2003

(86) PCT No.: PCT/IB03/01392

§ 371 (c)(1),
(2), (4) Date: Sep. 8, 2004

(87) PCT Pub. No.: WO03/075989

PCT Pub. Date: Sep. 18, 2003

(65) Prior Publication Data

US 2005/0188989 A1    Sep. 1, 2005

Related U.S. Application Data

(60) Provisional application No. 60/362,441, filed on Mar. 8, 2002.

(51) Int. Cl.
  *A61M 16/00* (2006.01)
  *A62B 7/00* (2006.01)
  *F16K 1/08* (2006.01)
  *F16K 31/02* (2006.01)
  *H02K 5/16* (2006.01)
  *H02K 7/08* (2006.01)
  *H02K 21/12* (2006.01)
  *H02K 1/22* (2006.01)

(52) U.S. Cl. ............ 128/204.21; 128/204.19; 310/90; 310/156.04; 310/268

(58) Field of Classification Search ............ 128/204.18, 128/204.19, 204.21, 205.18, 203.12, 203.14; 417/45, 423.12; 310/90, 90.5, 51, 268, 156.04
See application file for complete search history.

(56) References Cited

U.S. PATENT DOCUMENTS 5,245,995 A    9/1993    Sullivan et al. ........ 128/204.23

(Continued)

FOREIGN PATENT DOCUMENTS

EP    0 821 976    2/1998

(Continued)

*Primary Examiner*—Justine R Yu
*Assistant Examiner*—Kristen C Matter
(74) *Attorney, Agent, or Firm*—Westerman, Hattori, Daniels & Adrian, LLP.

(57) ABSTRACT

An apparatus to deliver air to a patient through a mask, including an air blower (33) where the impeller (5) is rotated by an electromotor including a rotor (3) and a stator (8), the stator having at least three sectors (8a, 8b and 8c), the rotation of the rotor being enabled by changes of the polarity of the sectors, each sector's polarity configuration constituting one step of the rotor's rotation, the apparatus including a driving unit (36) changing the sectors' polarity when the rotor is at its optimal position, so that the efficiency of the electromotor enables the blower to have fast accelerations and decelerations within one patient's breath step, the breath step consisting of one inspiration and one expiration.

27 Claims, 15 Drawing Sheets

U.S. PATENT DOCUMENTS

| | | | |
|---|---|---|---|
| 5,503,146 A | 4/1996 | Froehlich et al. | 128/204.23 |
| 5,508,575 A * | 4/1996 | Elrod, Jr. | 310/156.04 |
| 5,694,926 A * | 12/1997 | DeVries et al. | 128/205.24 |
| 5,744,921 A * | 4/1998 | Makaran | 318/254 |
| 5,875,783 A * | 3/1999 | Kullik | 128/204.18 |
| 5,970,975 A | 10/1999 | Estes et al. | 128/204.23 |
| 5,977,737 A | 11/1999 | Labriola, II | 318/599 |
| 6,152,129 A * | 11/2000 | Berthon-Jones | 128/200.24 |
| 6,401,713 B1 * | 6/2002 | Hill et al. | 128/204.21 |
| 2002/0000228 A1 | 1/2002 | Schoeb | 128/204.19 |
| 2002/0014239 A1 | 2/2002 | Chalvignac | 128/18 |
| 2005/0103339 A1 * | 5/2005 | Daly et al. | 128/204.18 |
| 2007/0119454 A1 * | 5/2007 | Berthon-Jones et al. | 128/204.23 |

FOREIGN PATENT DOCUMENTS

| | | |
|---|---|---|
| EP | 1 166 813 | 1/2002 |
| EP | 1 177 810 | 2/2002 |
| WO | WO 92/11054 | 7/1992 |
| WO | WO 98/57691 | 12/1998 |
| WO | WO 02/26305 | 4/2002 |
| WO | WO 02/053217 | 7/2002 |

\* cited by examiner $$VM = \frac{VPOWER}{2} + Vbemf$$

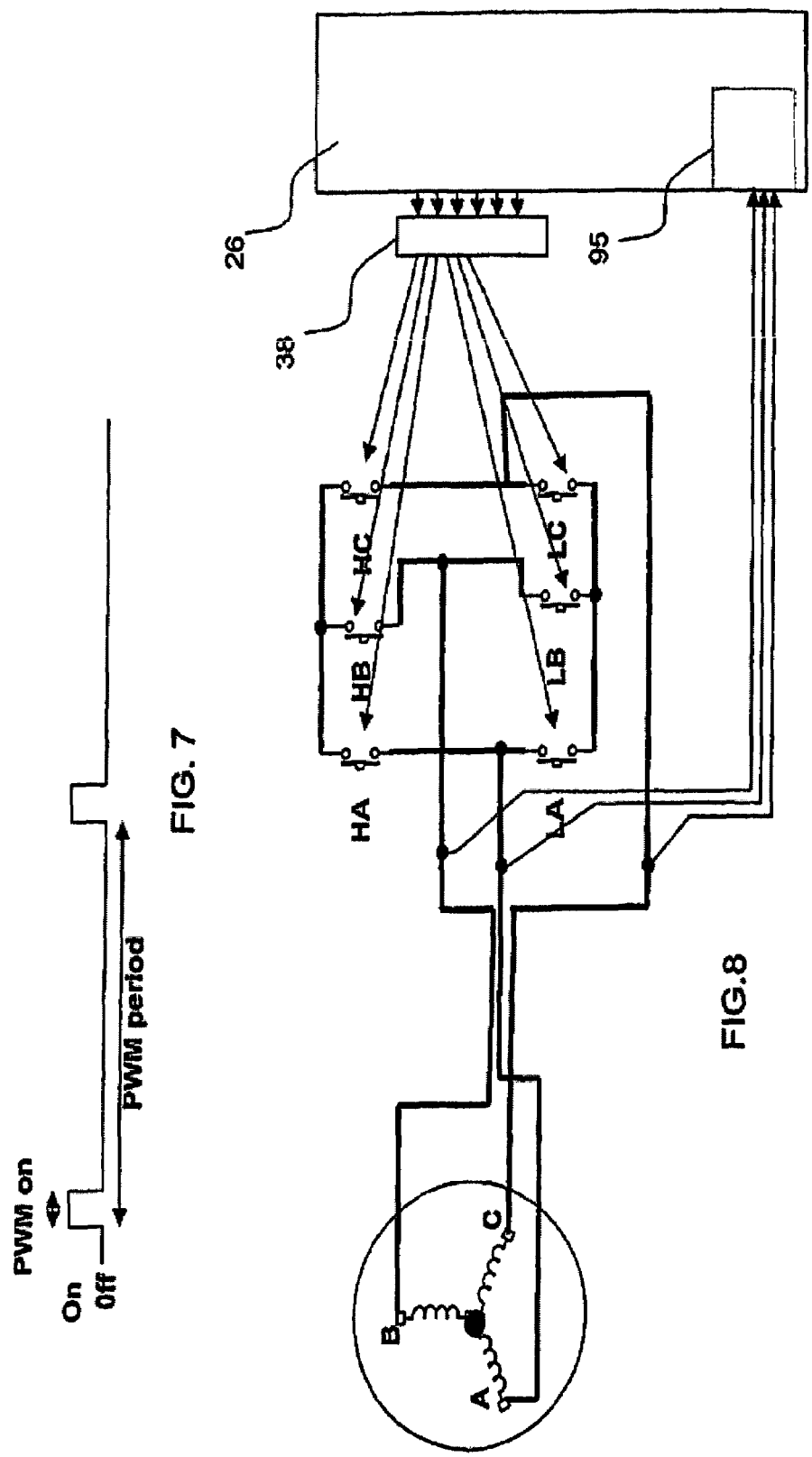

AIR ASSISTANCE APPARATUS PROVIDING FAST RISE AND FALL OF PRESSURE WITHIN ONE PATIENT'S BREATH

This application is a U.S. National Stage of International application PCT/IB03/01392, filed Mar. 10, 2003 and claims benefit of U.S. provisional application Ser. No. 60/362,441, filed Mar. 8, 2002.

TECHNICAL FIELD

The present invention concerns a medical apparatus to assist a patient respiration and more specifically an apparatus able to control the pressure of the air provided to the patient.

BACKGROUND ART

Some apparatus are used to provide patients with air. This is used in many treatments. More frequently it is used for patients with a breathing deficiency caused for example by the weakness of the breathing system or by obstructive apneas during the sleep. In those cases it is important to control the pressure of the air delivered to the patient. With respiratory insufficient patients, apparatus providing air at a higher pressure help to compensate the weakness of the patients lungs. In the case of patients suffering of sleep apneas, providing the air at a higher pressure removes the obstruction of the upper airways.

Several kinds of apparatus are used. The CPAP (Continuous Positive Airway Pressure) apparatus provides a constant pressure to the patient. An enhancement of the CPAP is adjusting the pressure delivered according to the detection of events (snoring, apneas, hypopneas, . . . ) for example, those apparatus will increase pressure (within bounds) if events are detected and will reduce pressure (within bounds) if no events are detected during a defined duration. Other apparatus operate with two different levels of pressure, one for the inspiration phase, the other one for the expiration phase. They treat the sleep apnea disorder as well as some respiratory insufficient patients. Those apparatus are composed of a centrifugal blower which provides the air. This blower comprises an impeller which is rotated by an electrical motor using the brushless technology. The rotor is a multi poles permanent magnet and the stator is an electrical magnet with several crenels each of them having a winding. The windings are alternatively connected to a power source so that the magnetic field changes in the stator crenels enable the rotor to rotate.

These apparatus require efficient motors. In order to operate sensors are precisely positioned on the stator to detect the position of the rotor. The sensors are connected to a processor in order to provide the information concerning the position of the rotor. The processor is then able to drive the windings phases according to the rotor position. The efficiency of those motors is highly linked on the precision of the positioning of the sensors and the reliability of the system is linked to the reliability of the sensors. Those sensors detect the position of the rotor by the variations of the magnetic flow and thus their reliability depends also on their bandwidth. Standard sensors have usually a 10 kHz bandwidth and thus are not able to operate correctly at high speeds. Higher speeds can be provided by using sensors with a higher bandwidth but those sensors are expensive and still have a speed limitation. In fact the faster the rotor rotates the worse the detection is accurate, the less the motor is efficient. Sometimes the system can even stall. Because these problems of positioning and reliability, those air providing apparatus which are using these sensors do not use high speed motors. The provided pressure is proportional to the impeller rotation speed and to the size of the impeller. Thus, in order to have the required pressure the size of their impeller is increased. Mainly those apparatus use big impellers having a diameter comprised between 70 and 100 millimeters. Such impellers imply high inertia, thus preventing quick speed changes.

Moreover, in the case of a CPAP that does not require pressure changes within a breath, to have a well regulated pressure at the patient interface, these apparatus are requiring the use of a 22 millimeters diameter tube as the pressure drop within such a tube is negligible but the use of a smaller tube will not guarantee the pressure regulation A within acceptable bounds.

In the case of two levels of pressure apparatus, as changing the blower speed within a breath is impossible to achieve due to the high inertia, the highest level is delivered by the blower and the lowest is managed by using pneumatic valves, pressure dividers or alternative methods.

The size of the impeller, the sensor positioning and attachments and the number of wires required increase the size of the blower and thus of the apparatus. Furthermore the precise positioning of the sensors complicates the assembling of the motor implying an increase of the cost.

In US 2002/0000228, the inventors have used a way to obtain fast accelerations and decelerations which does not relies on the positioning of the rotor. US 2002/0000228 discloses a blower for an air assistance apparatus. The blower operates with an electric motor. The polarity of the stator's sectors are changed by a driving unit to achieve fast accelerations and decelerations in one patient's breath step. This result is obtained by using a compressor wheel with a very low mass and by holding the wheel without contact in the radial compressor. This system requires a lot of precision when assembling the motor to obtain the magnetic fields that will hold the wheel without contact in the compressor. The rotor position can not be determined.

Document U.S. Pat. No. 5,977,737 relates to a way to enhance the accuracy of the motor functions. The improvement of the accuracy is carried out by predicting the motor current. There are no means for sensing the motor current. The prediction of the motor current is made by using different parameters such as motor inductance, motor and driver resistance and the back-electo motor force (back-EMF) value. The motor's position may also be included as one of the parameters. Using these parameters the current is calculated. This allows the determination of the pulse widths to be applied to various inputs to the driver circuit. The back-EMF is not used to determine the rotor's position and to change the sector's polarity in respect of this position. U.S. Pat. No. 5,977,737 does not disclose a way to determine the rotor's position. The aspect disclosed by U.S. Pat. No. 5,977,737 is a more-accurate delivery of current and not a way for increasing the electro motor's efficiency. This document thus does not provide any indication to obtain fast accelerations and decelarations within a patient's breath.

SUMMARY OF THE INVENTION

The invention object is to provide an apparatus able to deliver air to a patient at a controlled pressure in such a way that the pressure could be modulated within a breath according to the breath pattern and according to events detected from the patient.

Another object is to provide an apparatus enabling the use of smaller diameter tubes than the standard 22 mm.

Another object of the invention is to provide an apparatus with a lower size, being more power efficient and to improve comfort, to be as quiet as possible.

A further object is to provide an apparatus easier and cheaper to assemble.

The subject of the invention is an apparatus able to deliver air to a patient at a controlled pressure in such a way that the pressure could be modulated within a breath according to the breath pattern and according to events detected from the patient.

This is obtained by a very efficient centrifugal blower which is able to rotate at high speed (up to 50000 round per minute) and to decelerate and accelerate very quickly (±10 hPa in 30 milliseconds). This efficiency is obtained by having a very light and small diameter impeller, preferentially 50 mm, and having preferentially a weight of 10 grams. This efficiency is obtained in the motor by detecting the optimal rotor position by measuring the back electro motor force (BEMF) generated in the blower motor. In respect of the BEMF detected a computer or processor is able to know the position of the rotor and accordingly will change the phases of the stator branches.

The use of this technology avoids using sensors which enable the rotor to rotate at high speeds without malfunctioning. Tubes of a 15 millimeters can be used without pressure drops. The small size of the blower enables to reduce the whole apparatus and enables to create an ambulatory apparatus.

An other implementation of this technology is that a toroidal stator is used. This further increases the efficiency of the blower and its size. This toroidal stator is also easiest and cheapest to assemble.

Another side of the invention relates to its ability to communicate with its power supply.

An implementation of this invention is to be able to modulate the pressure of the air provided. This modulation occurring within one inspiration or expiration, which is enabled by the capacity of the apparatus to provide fast accelerations and decelerations.

Also the apparatus is able to react to events occurring in patients breathing and in response to modify the provided air pressure, possibly to adopt a given shape of the pressure to patient's mask being a function of time according to the frequency of the patient's breathing parameters. The apparatus according to present invention has the capacity to provide such a modulation within one single breath.

BRIEF DESCRIPTION OF FIGURES

FIG. 7 represents of the Pulse Width Modulation in function of time, FIG. 8 represents the connections which enable to control the rotor rotation.

DETAILED DESCRIPTION OF THE INVENTION

Figure 1:
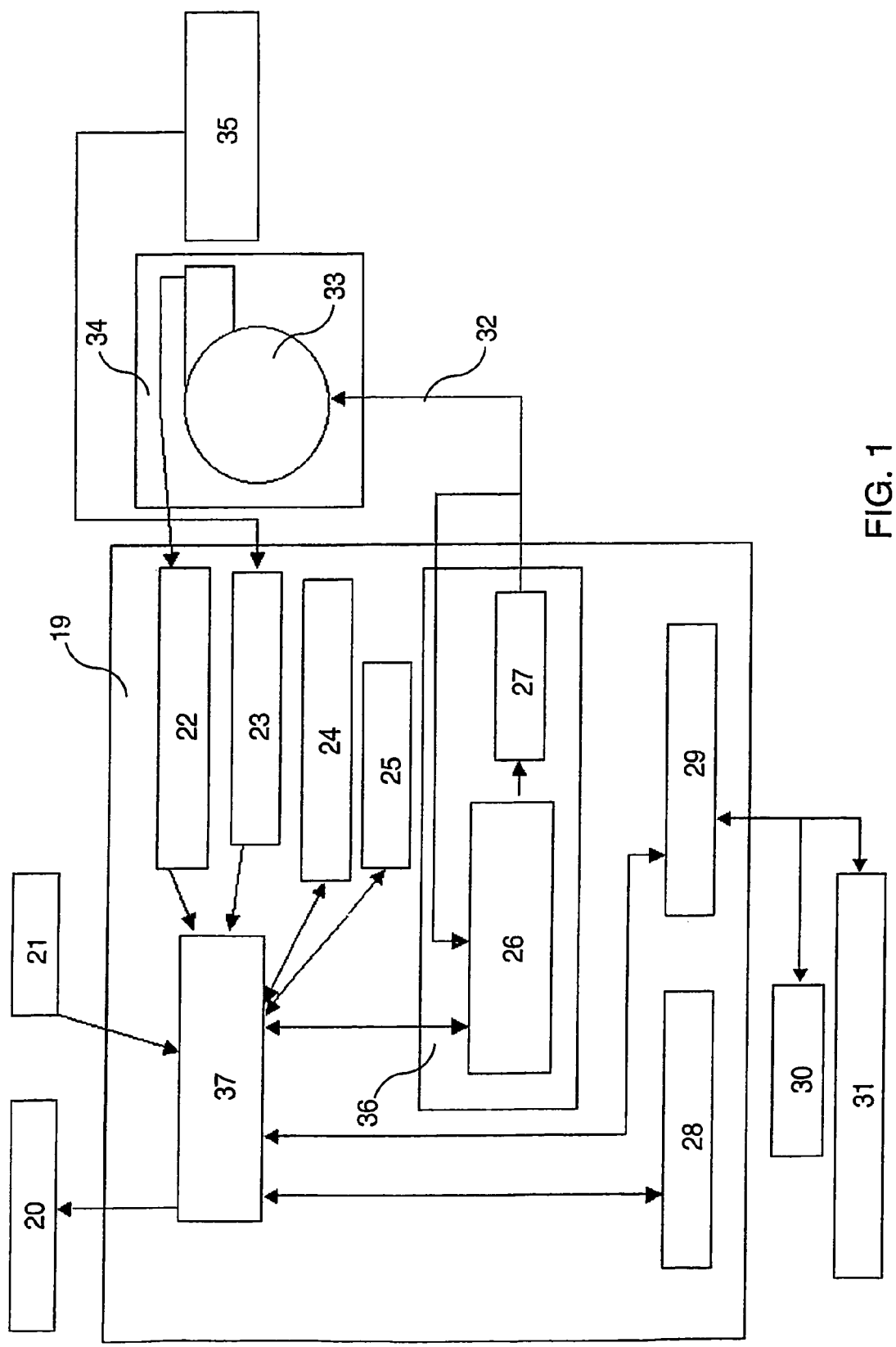
FIG. 1 represents the connections between the elements of the apparatus according to the present invention.

The apparatus according to the present invention provides a patient under treatment with air under controlled pressure. As represented in FIG. 1, the apparatus includes a high speed and low inertia centrifugal blower 33, an acoustic assembly 34, a computerized electronic board 19, a graphical display 20, a keyboard 21, and a sensor 35 connected to the a tube first extremity, connected to the patient's mask. This tube is connected to the blower 33 on its second extremity, but as the FIG. 1 represents the alimentation and the communication connections, the tube has not been represented.

In a preferred embodiment, the computerized electronic board 19 includes:
- means 23 and 35 for sensing the pressure at the patient's mask,
- means 22 for sensing the pressure at the centrifugal blower 33,
- a non volatile memory 24 used to store patient compliance data's and measurements,
- a real time clock 25 used to time mark the events,
- a pressure control unit 37 to adapt the pressure provided at the mask,
- an Infrared bi-directional data communication system following the IrDa standard 28 used to allow wireless communications with the apparatus,
- a power supply manager 29,
- a motor driving system 36 which comprises a micro controller 26 and a power stage 27 connected to the centrifugal blower 33 by three wires 32.

The computerized board 19 is provided with energy by a battery pack 30 or an external DC power supply 31.

These different elements are connected each other as represented in FIG. 1 by the links with a single arrow on one or two extremities of a link. This can be an electrical or data's connection.

The motor driving system 36 is a mean for optimally using the efficiency of the electric motor of the air blower.

The adaptation of the air flow to a patient requires efficient motors. This is why sensors were used to know the position of the rotor, in order to change the rotor when at its optimal position. But as explained above, the sensors of prior art have several downsides.

The apparatus according to present invention as the capacity to precisely determine the rotor's optimal position, so that the efficiency of the electro motor enables the blower to have fast accelerations and decelerations within one patient's breath.

The solution provided by the invention is that instead of directly detecting the position of the rotor by the mean of sensors, it is detect by sensing the back electro motor force (BEMF) generated by the motor. This BEMF is detected on one branch of the stator which has three sectors.

Figure 2:
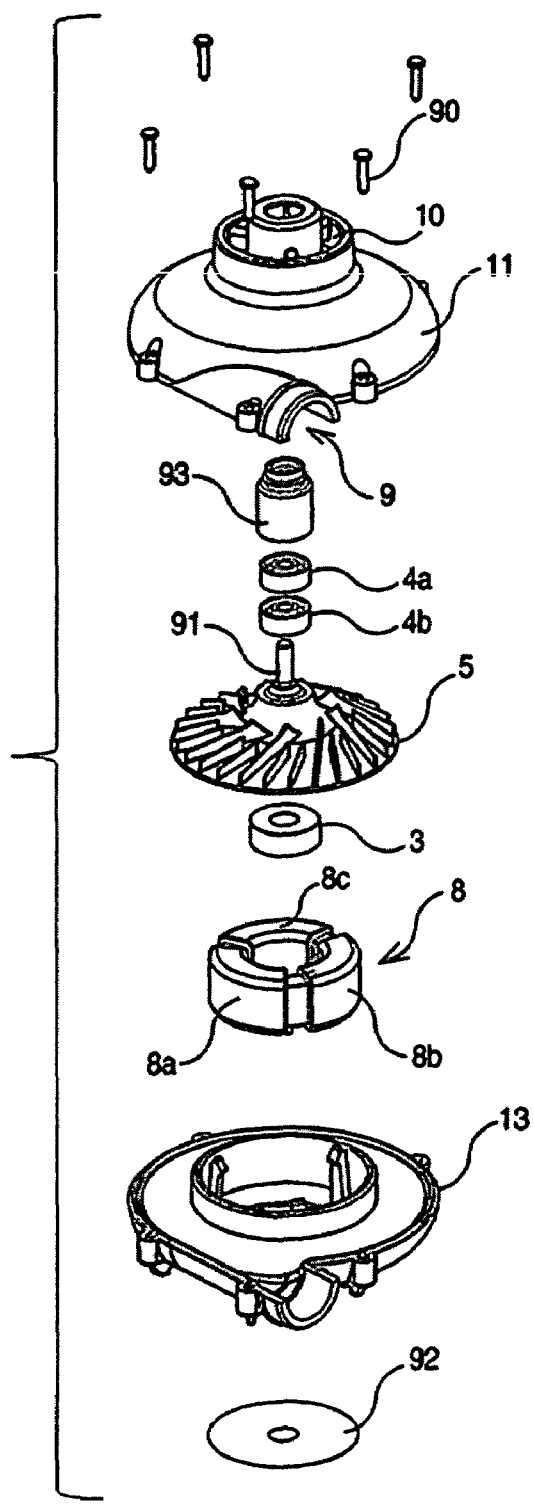
FIG. 2 represents the assembling of the centrifugal blower of the apparatus according to the present invention.
Figure 3:
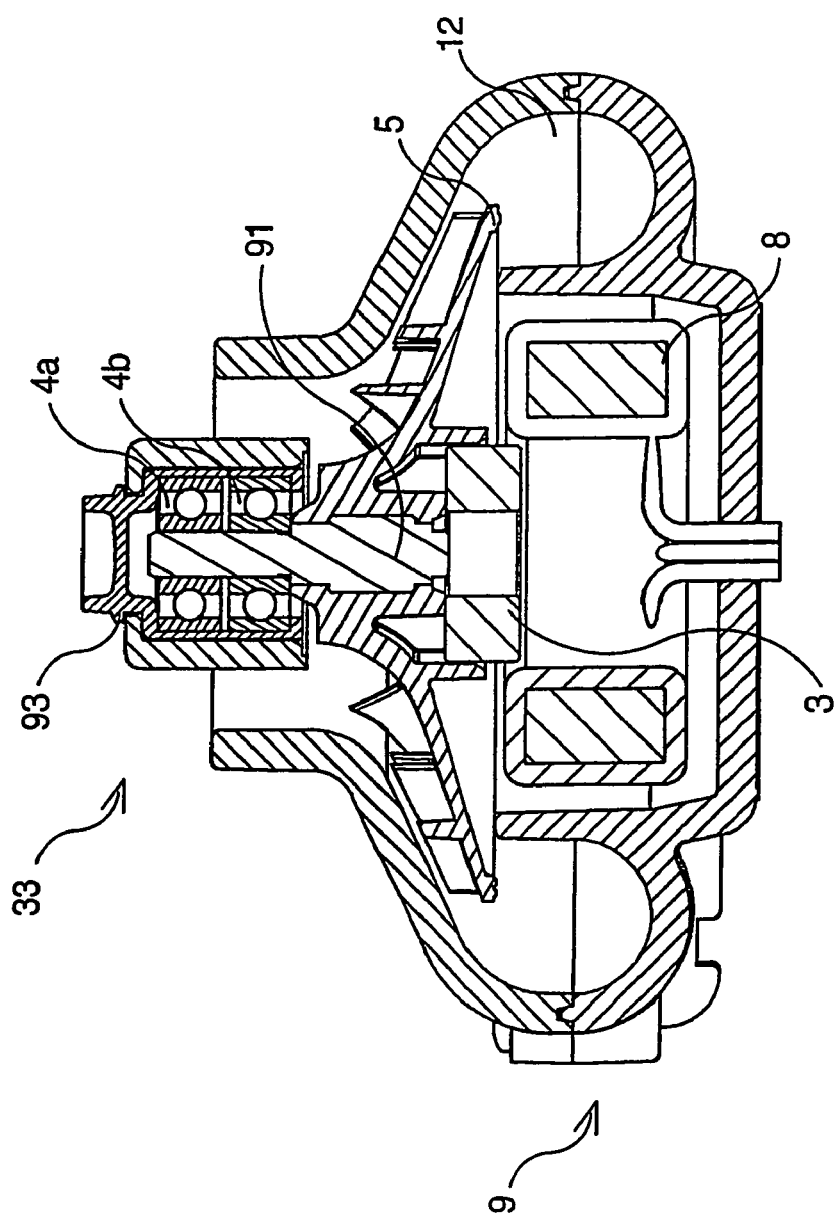
FIG. 3 represents a section of the blower of the apparatus according to the present invention.

The air blower as represented in FIGS. 2 and 3 is composed of:
  a top cover 11 which comprises an air inlet hole 10,
  an impeller/rotor 2 subsystem including two high speed bearings 4a and 4b, a rotor 3 which is permanent magnet with two poles and a twenty seven blades impeller 5, of for example 47 mm diameter,
  a bottom cover 13,
  a three stator 8 with three sectors 8a, 8b and 8c.

FIG. 2 represents also the screws 90 to fix the bottom and top covers together. Also is represented a sticker 92, which is added in the embodiment of blower represented to avoid air leakage.

When assembled the stator 8 and the rotor 3 composed the electric motor which rotates the impeller 5 which is attached to the rotor. The impeller rotation attracts air trough the air inlet and compresses it in the chamber 12. The air is blown under pressure through the air outlet 9. The tube to patient's mask is connected to the air outlet 9.

Figure 4A:
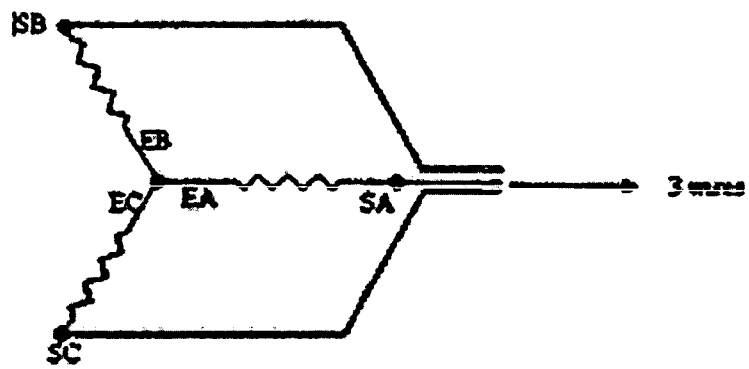
FIG. 4a is a symbolic representation of the three stator sectors connected to the power source.
Figure 4B:
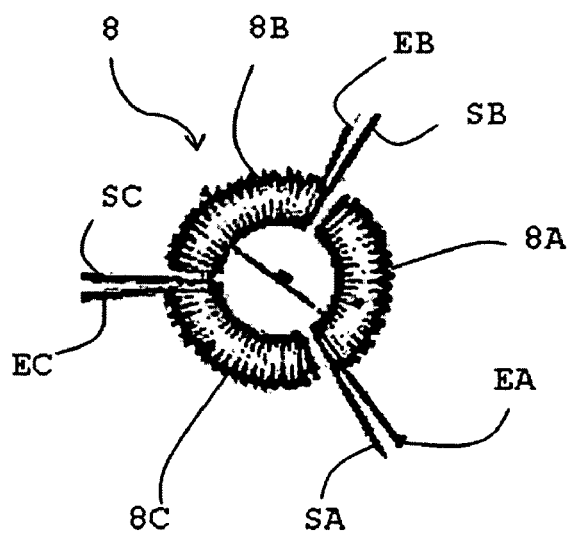
FIG. 4b represents a preferred embodiment of the stator.

In a preferred implementation, represented in FIG. 4b, the stator 8 is a toroidal stator composed of three sectors which are coils 8A,8B, and 8C. Each sector has two extremities. The coil 8A has two extremities SA and EA. the coil 8B has two extremities SB and EB and the coil 8C has two extremities SC and EC. As it is represented in FIG. 4a, the two extremities of each coil are grouped and join to a wire. This enables the stator to require only three wires to be connected.

Figure 5:
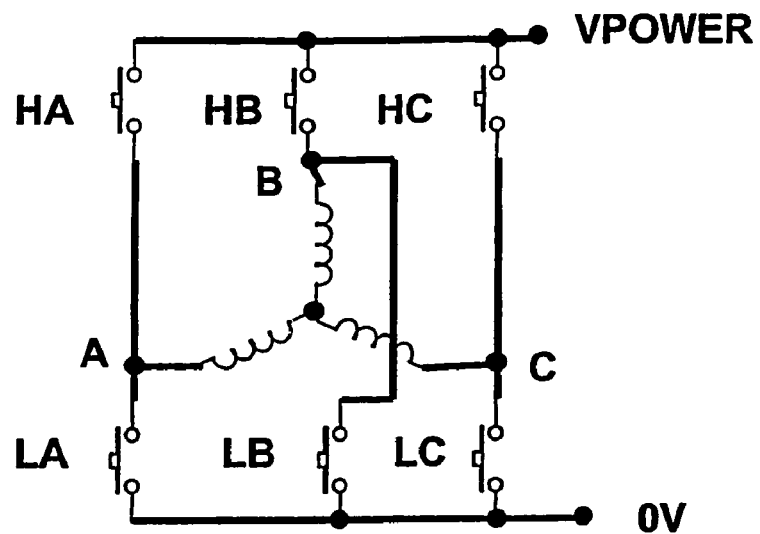
FIG. 5 is a symbolic representation of the different switches which connect the stator sectors to the power source.
Figure 6:
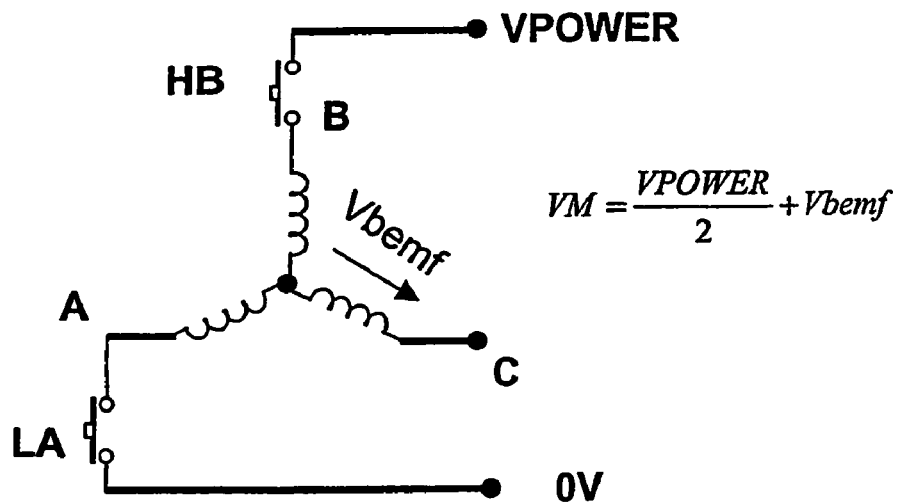
FIG. 6 is a simplified representation which shows one configuration of switches setting.

The FIG. 5 represents schematically the way the stator 8 with three sectors is connected to the power stage 27 which provides the motor with energy. Each of the three stator sectors 8a, 8b and 8c, is connected to respectively A, B or C. The switches HA, HB and HC (switches H) connect the positive plot of the power supply to each respective branch of the stator A, B and C. Each of these branches corresponds to one stator sector 8a, 8b and 8c. In the same way the switches LA, LB and LC (switches L) connect to the negative plot (0V) of the power supply to the respective branches A, B and C of the stator. The motor functions by rotation steps. In each of these different steps, different phases are applied to each point A, B, C in order to rotate the rotor. FIG. 6 represents one of these steps. In this figure, switches LA and HB are switched on applying the tension VPOWER delivered by the power stage 27 between branch B and A. The switches connected to C are switched off, thus enabling to measure the tension VM between C and the negative plot. In these conditions, this voltage obeys to the formula:

$$VM=(VPOWER/2)+Vbemf$$

wherein Vbemf represents the value of the BEMF.

This enables the micro controller 26 to measure the BEMF. The best instant to change the phase is when the rotor 3 arrives in the optimal position, which is when the rotor magnetic field and the magnetic field between A and B are in a situation of opposite polarity. Before the rotor reaches this position, the BEMF will be positive; if the rotor pass this position, the BEMF will be negative. At the instant the rotor is at the optimal position the value of the BEMF equals zero. Thus, when the zero value is detected on C the second micro controller 26 sends orders to configure the switches positions to change the configuration of the stator branches polarity. Each change causes the rotor rotation.

This system enables the motor to be very efficient and thus enables high speed rotation and quick accelerations. By avoiding the use of sensors depending on their position, the apparatus according to present invention enables to rotate easily at a high speed. This high speed rotation enables to reduce the size of the impeller while providing the same pressure. The impeller as consequently a lower inertia this enables to further increase the acceleration of the motor.

But in breath support it is also very important to provide good decelerations. When the tension is applied on one sector of the stator 8 the corresponding switch H is on. The tension is preferentially applied with pulses, such a tension is called a Pulse Width Modulation or PWM. This means that during a first duration of time the switch H is on, and that during a first duration of time the switch H is off, these two steps consisting in what is called the PWM period. Then H is switched on again and a second PWM period begins. The FIG. 7 represents the PWM value related to time evolution. Because of the short time of the PWM period (typically between 50 and 100 µs), the tension in the system PWM is given by the formula:

$$PWM=(PWM\text{"on"}/PWM\text{"period"})\times VPOWER$$

VPOWER being the tension the driving unit is provided with.

For example, during the PWM period when HA is off, if LA is also open, the system functions correctly at high speeds and with fast accelerations but has no possibility of fast decelerations. To decelerate it is required to decrease the PWM value, which is done by shortening the period when the tension is applied (PWM"on" with the switch HA on). Thus the tension applied will decrease but the BEMF will not decrease immediately. None of the switches settings is allowing the BEMF to be drawn to either rail of the power supply. This means that when PWM reaches the zero value and when the switch HA is on, it will be similar to have a left opened free wheeling motor which only breaks by mechanical bindings (in bearings for example) and according to the airflow load (airflow driven out). To implement the system and provide fast decelerations, a solution is to switch the LA switch on during the period when HA is a off. Thus the current generated by the motor will be sent via LA to the system. In case of PWM decrease the motor will provide a motor braking which enables a fast deceleration.

As an implementation of the invention is to switch on one of the L switches during the PWM period and to switch the switch H of the same branch off at the same time, a limitation appears if having PWM on both sides of a branch during the transition time, physical switches such as MOSFET transistors are having delays to change their state from ON to OFF or OFF to ON. This means that the transitional condition where the two switches, L and H, of the same branch are on, can occur resulting on a direct short cut of the power supply. The implementation thus requires to generate a dead time period between the H switch switching OFF and the L switch of same branch switching ON. This can be generated by a software and a micro processor comprised in the driving unit.

The FIG. 8 represents how the stator and the switches are connected to the micro controller 26. As represented in FIG. 8, the stator is connected to the switches set by only three wires, each stator sectors being connected on A, B and C as described above. Each point A, B, C is connected to the micro controller 26 which enables to measure the BEMF as described above. The micro controller 26 send the numerical orders to an adapter 38, which converts these orders into a position of the corresponding switch, so that the driving unit is enabled through a micro controller's software to switch each switch off or on.

The following table 1, shows the functioning of the controller 26 during one rotating sequence (one complete rotation of the rotor).

TABLE 1

| Cxout | STEP | | | | | |
|---|---|---|---|---|---|---|
|  | 1 | 2 | 3 | 4 | 5 | 6 |
| 0(HA) | PWM | PWM | 0 | 0 | 0 | 0 |
| 1(LA) | !PWM | !PWM | 0 | 1 | 1 | 0 |
| 2(HB) | 0 | 0 | PWM | PWM | 0 | 0 |
| 3(LB) | 1 | 0 | !PWM | !PWM | 0 | 1 |
| 4(HC) | 0 | 0 | 0 | 0 | PWM | PWM |
| 5(LC) | 0 | 1 | 1 | 0 | !PWM | !PWM |
| BEMF ON: | C | B | A | C | B | A |

In this preferential mode as the stator has three sectors and as the rotor is a dipole magnet, the sequence comprises six steps corresponding to the six different ways of applying the polarity to the stator branches in order to rotate the motor in one sense. The state of each switch is represented in respect of each step. For example in step 1, HA is switched on during the PWM on time (and off during the rest of the PWM period), LA is switched on during the rest of the PWM period (noted !PWM). HB, HC, and LC are switched off and LB is switched on. During this step, A has got the positive polarity and B the negative polarity. The BEMF is measured on C. This measure is sent to the micro controller 26. When the BEMF reaches the 0 value, then the command are operated to gave the instructions to switch the switches in the configuration of step 2. In step 2 the positive polarity stays on A, the negative polarity is on C, enabling a 60 degrees rotation of the rotor. The BEMF is measured on B, and so on for each step.

Thus, the efficiency of the motor driving system 36 allows very fast and accurate accelerations and decelerations of the motor. As the rotation of the motor rotates the impeller and as the impeller rotation speed is a function of the pressure provided by the blower, this efficiency enables fast rise and fall of pressure. Typically under normal airflow load conditions, the blower will rise from 1 hPa (hecto pascals) to 30 hPa in less than 200 milliseconds under the same conditions, the blower will drop from 30 hPa to 1 hPa in the same duration. The rise or fall can be of more than 10 hPa in 30 to 60 milliseconds.

For the intended use of the apparatus, those performances are giving to the device enough latitudes to accomplish an enhanced pressure regulation at the patient mask and a multi level of pressures within breaths without the requirement of additional valves.

This provides the maximum efficiency of motor rotation, and enables it to rotate at high speed (more than 50000 rounds per minute) and to have fast acceleration or decelerations, that is to say at least a.

In the preferred embodiment the stator as only three sectors. Even if it would be more complicated, it could also be used stators with more sectors. For example a six sectors stator could be used with a rotor being a magnet with four poles.

Figure 10:
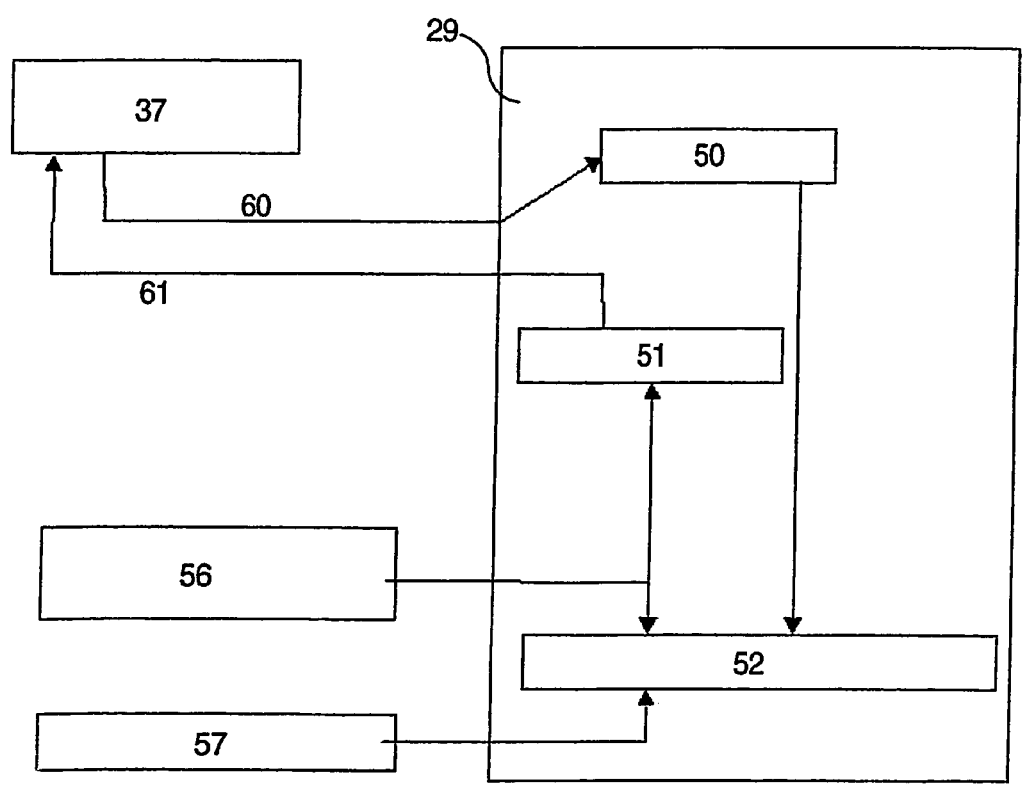
FIG. 10 represents the communication of the data in the apparatus.

In a preferred embodiment the apparatus has a power supply manager 29 which is connected to a battery pack 30 or to the power supply sector via an external plug 31. The power supply manager comprises a communication module which enables to avoid expensive connectors and cables. This module is used to transmit data trough the power source wires. As represented in FIG. 10, the pressure control unit 37 transmit a binary data flow 60 to a Frequency Shift Keying (FSK) modulator 50 which transforms these binary data in a modulation of the tension frequency of the tension applied on the voltage controlled current source 52. The external power supply is connected on the voltage controlled current source 52 with its 0V plot 57 and its positive plot 56, so that the voltage controlled current source 52 transmit voltage frequency and possibly the modulation corresponding to the data. In the same way when a modulated voltage is applied by other modules or sensors on the positive plot 56, a FSK demodulator 51 will convert the voltage frequency modulation into binary data 61 and transmit them to the pressure control unit 37. This voltage is transmitted by the positive plot 56, so that each sensor or module connected to the power source is able to receive or transmit information.

Figure 11:
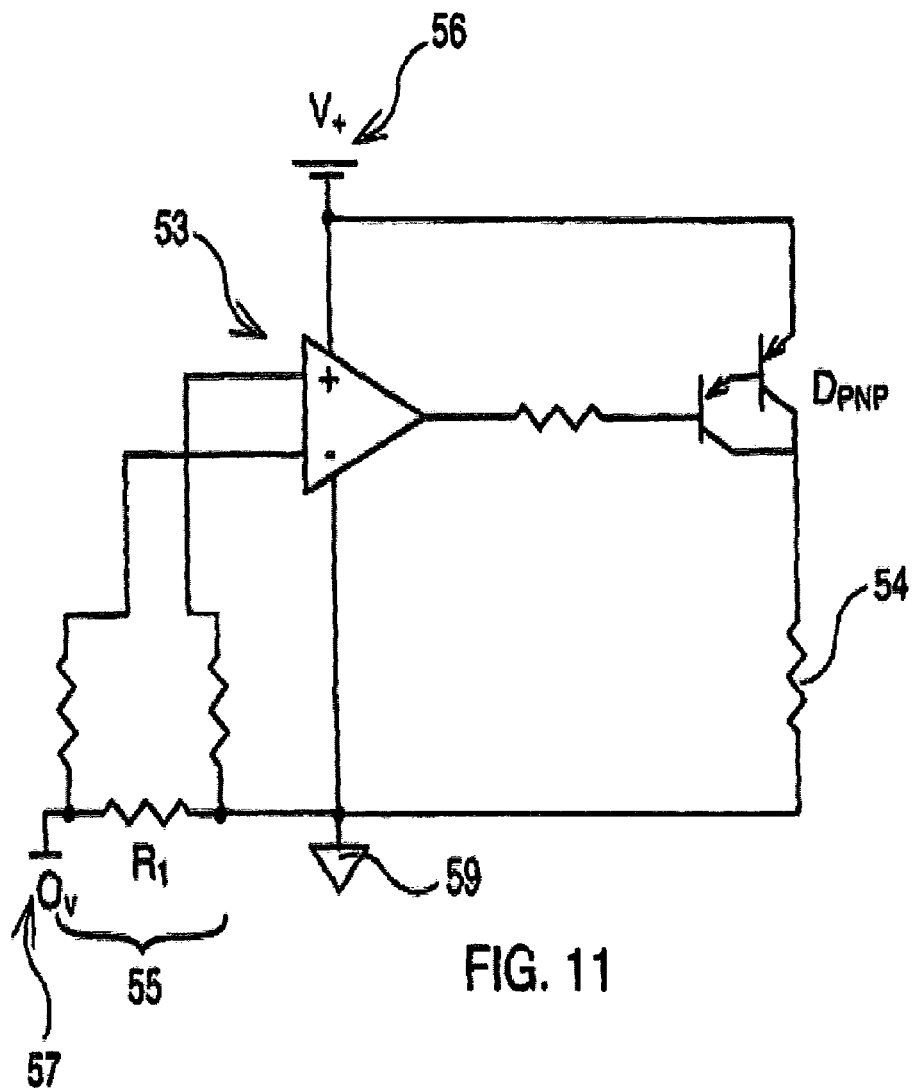
FIG. 11 represents the electric scheme of the load control module of the apparatus according to the present invention.
Figure 12:
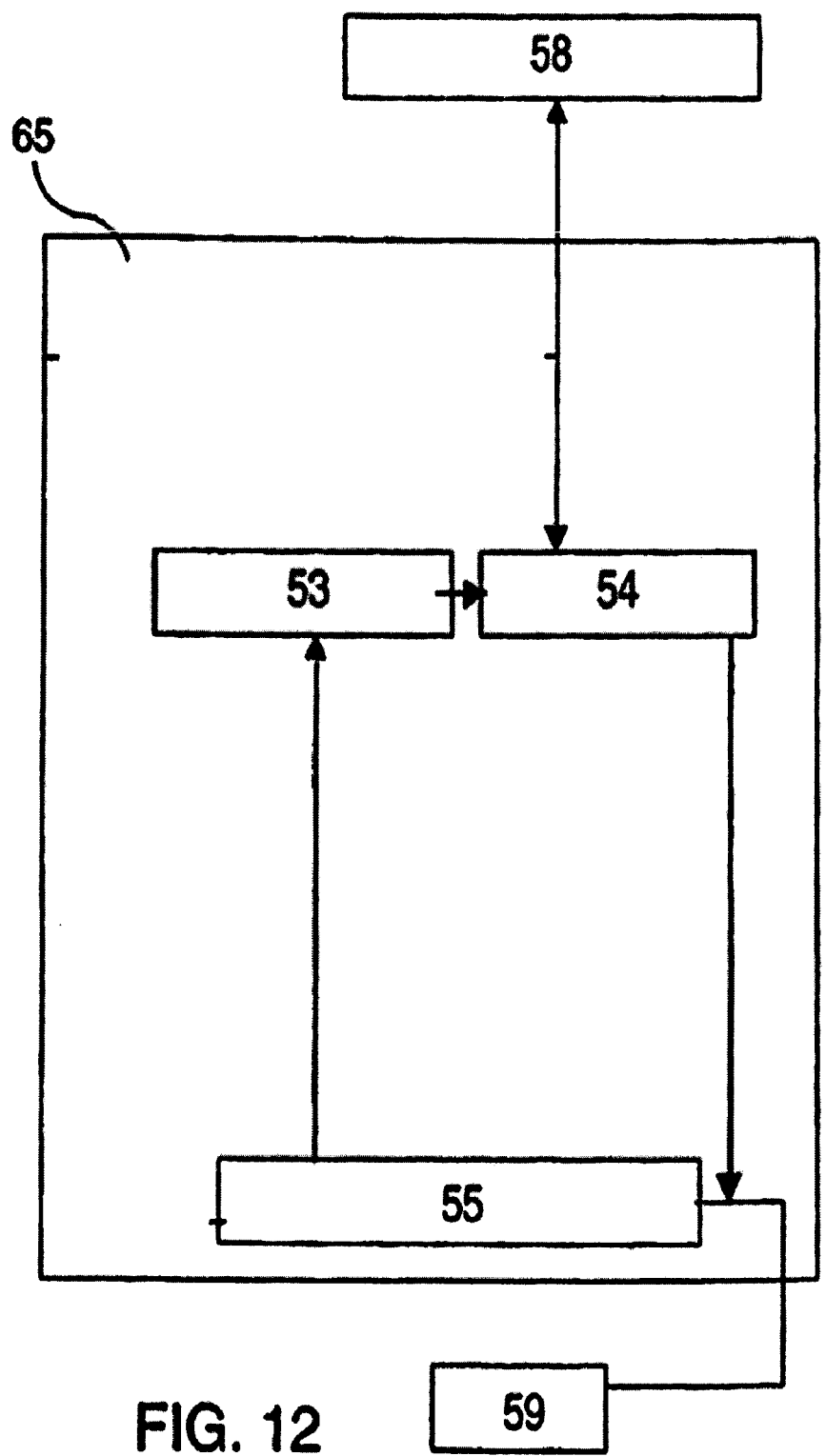
FIG. 12 represents the process of the load control of the apparatus according to the present invention.
Figure 13:
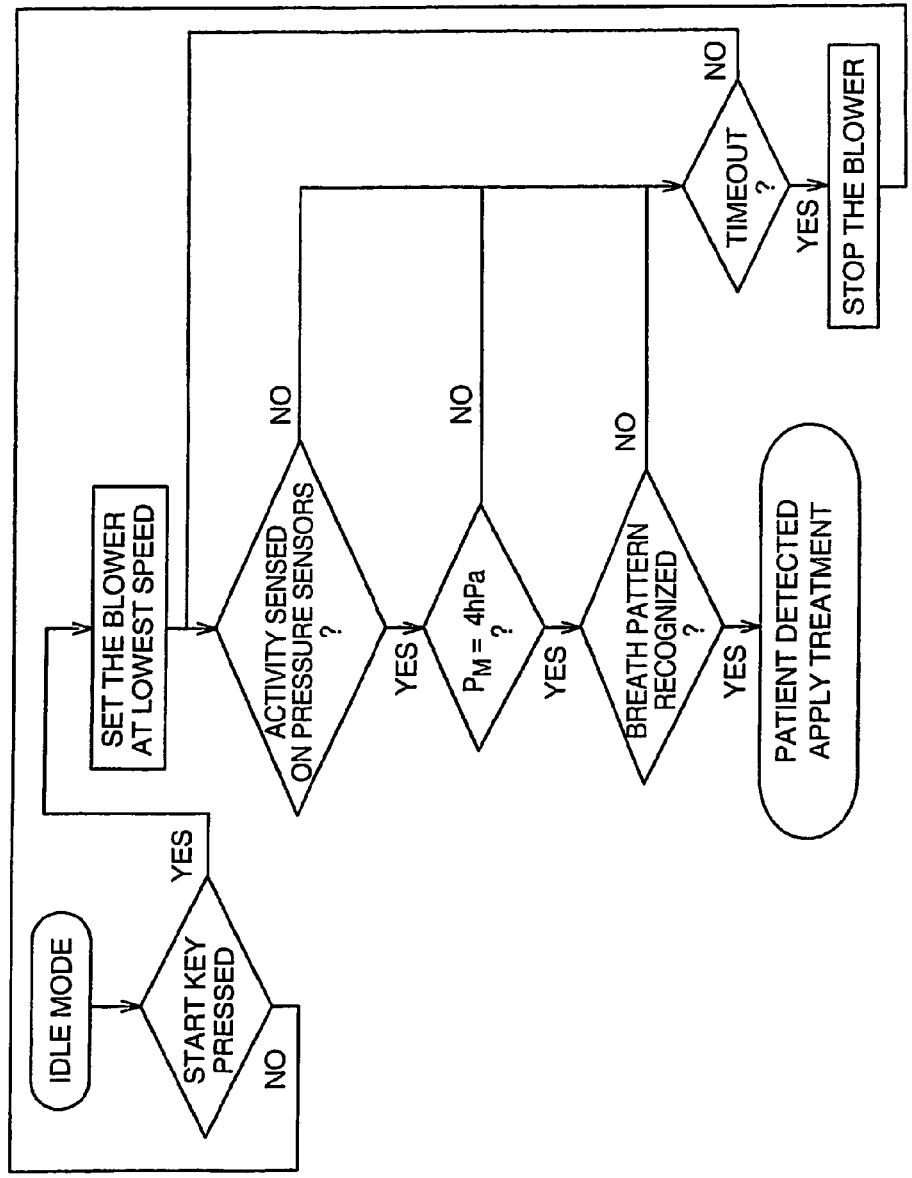
FIG. 13 represents a starting operating process of the apparatus according to the present invention.

In a further embodiment, the power supply manager 29 can comprise a load control module. The high speed centrifugal blower 33 has a motor 8 and 3 and regardless the motor technology, when a slowdown of the motor is required it induces a negative current from Ground to positive plot of the power supply, because the motor in that condition acts as a generator. If the motor decelerates, as for example described above with the implementation for enabling fast decelerations, this negative current is generated back into the system and will be sent into the power supply. When the power of the power supply only delivers energy to this apparatus and as a power close to the apparatus consumption power, serious damages can occur. The load control module aim is to prevent those downsides. As represented in FIG. 12 and 13, this load control module 65 comprises a current sensor 55, preferentially a 0.1 ohm resistor $R_1$ connected to the external power supply and to a comparator 53, the load control module 65 further comprising a load resistor 54 which can be connected by switches to the positive power supply 58 and to the ground 59. The comparator 53 is connected to the load resistor 54. The current sensor 55 provides the comparator 53 with the value of the current, so that when this value is negative the comparator 53 switches the load resistor 54 on between the positive power supply 58 and the ground 59 by the way for example of a Darlington PNP, or $D_{PNP}$, thus allowing the excess of negative current to be drawn in the load resistance 54 thus allowing the dissipation of the energy generated by thermal effect. Such device is particularly useful in the present invention but is not necessary and could be applied in other breath assisting apparatus like CPAP. The electric scheme of this implementation is represented in FIG. 11.

Preferentially, the apparatus according to the present invention further comprises bearings 4a and 4b and a bearing holder 93. The impeller 5, said rotor 3 and the impeller's shaft 91 are fixed together, said bearings being fixed to said axis and being hold inside the bearing holder. Thus the impeller, the rotor and the bearings inner ring rotate together with the shaft. The bearings outer ring being hold in the bearing holder, which is fixed in the apparatus. Instead of being centered inside the stator 8, the rotor is shifted outside the stator 8, preferentially at an equal distance of each of the three stator sectors 8a, 8b and 8c, so that the stator also generates on the rotor 3 an axial force oriented along the impeller's shaft 91, thus generating a preload on the bearings 4a and 4b. On bearings, a preload is required to operate smoothly and quietly. This further increases the motor efficiency. An other advantage is that it avoids the use of springs to generate the preload on the bearings.

The BEMF detection for controlling the blower motor allows high speed of impeller rotation. One advantage is that the noise gets in higher frequencies. This enables to insulate the blower with a smaller box 34 and enables to have less noise. By preferentially increasing the number of blades the apparatus according the present invention further moves the noise of the apparatus at higher frequencies. This number of blades is comprised between 14 and 45, preferentially 27. It is preferred to have an impair number of blades.

Figure 9:
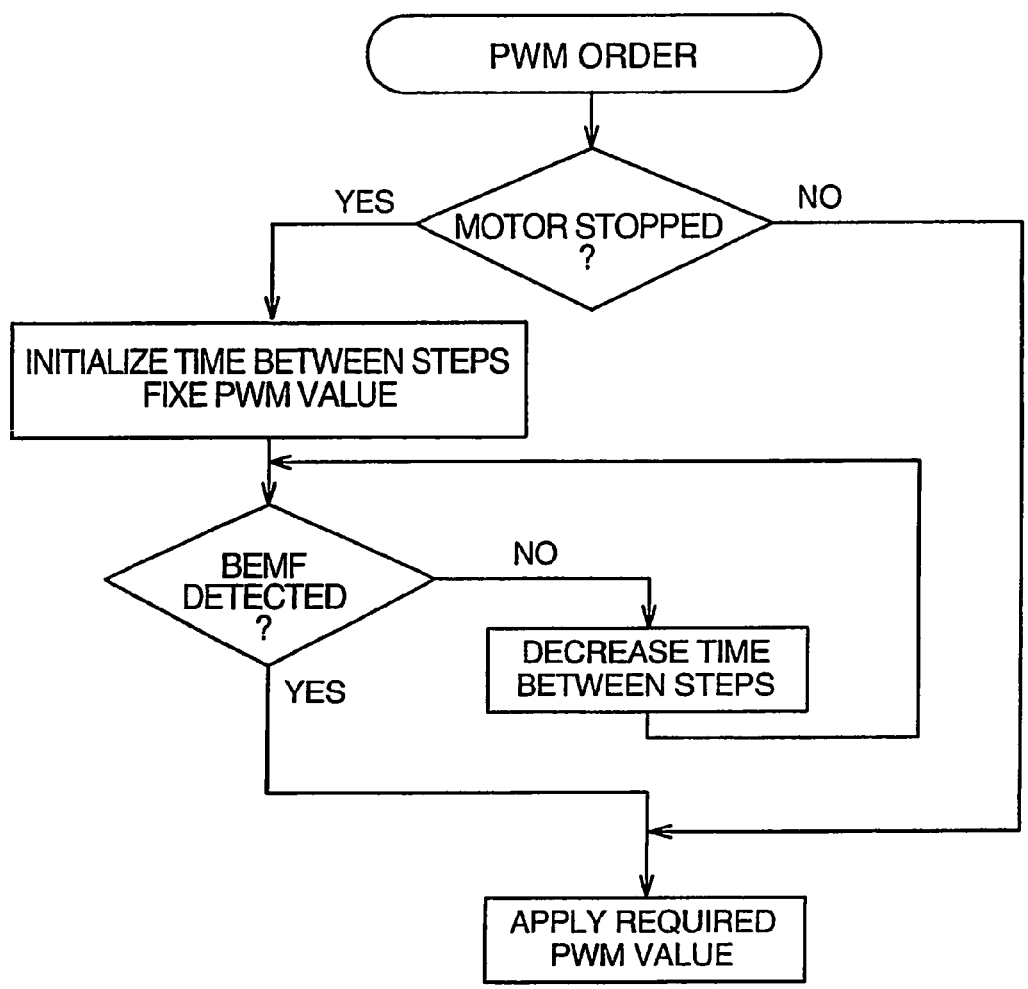
FIG. 9 represents the process to start the motor functioning.

An implementation of the present invention is to force the rotor 3 to rotate at a speed high enough to enable the BEMF to be detected. To this aim, when receiving a PWM value the micro controller 26 will follow the process as represented on FIG. 9. If the motor is not stopped then a request to apply the tension PWM value to the stator 8 is sent. If the motor is stopped, the micro controller 26 initializes the time between the rotor's rotation steps, these steps consisting in changing the phases of the stator branches. In that case, the micro controller 26 also fixes the PWM value. This means that until the BEMF is detected, the changes of phases depend on time and not on a BEMF detection. The micro controller 26 keeps on decreasing the time between the changing phases steps, until the BEMF is detected. When the BEMF is detected, the tension PWM value corresponding to the pressure required is applied. The apparatus function at this time with BEMF detection.

Another advantage of a BEMF detection is that the fastest the motor will turn, the more precise the BEMF detection will be resulting on an increase of efficiency.

An other embodiment of the invention is to obtain the stator 8 by using a strip wound cores with a high grade thin silicon steel. It is known that to improve stator efficiency the number of laminations have to be high to reduce core losses. The classical solution in motor design is to slice the stator in a high number of laminations with a thin isolation. According to the present implementation another method is used to obtain the stator: using a strip wound technique allowing to go to 0.05 mm thickness of the steel. This technique used in toroidal transformer has been here adapted to the apparatus Another advantage of the invention is that, the high rotation speed and quick rise time and fall time also enables to use tubes of a smaller size. Historically CPAP and respiratory assistance devices are using 1.8 m long, 22 mm outside diameter tubing, because the pressure drop on those tubes are negligible (0.7hPA for 1 l/s airflow). Pressure drops are happening during inspiration and, during expiration, pressure is increasing. In that case it is important that the pressure of the provided air does not change too much; this is the reason why 22 mm diameter tubes are used. The downsides of those tubing's are size and weight. It can be interesting to use smaller tubes given the reduced size of the apparatus. The downside of a reduced diameter tubing is the fact that significant pressure drops are occurring. Given the light weight of the impeller/rotor 2 combined with the efficiency of the motor driving system 36 and the load control of the power supply manager 29 allowing very fast and accurate accelerations/decelerations, the apparatus according to the present invention is able to compensate those pressure drops thus allowing the use of smaller tubing's (i.e. 15 mm outside diameters).

Figure 14:
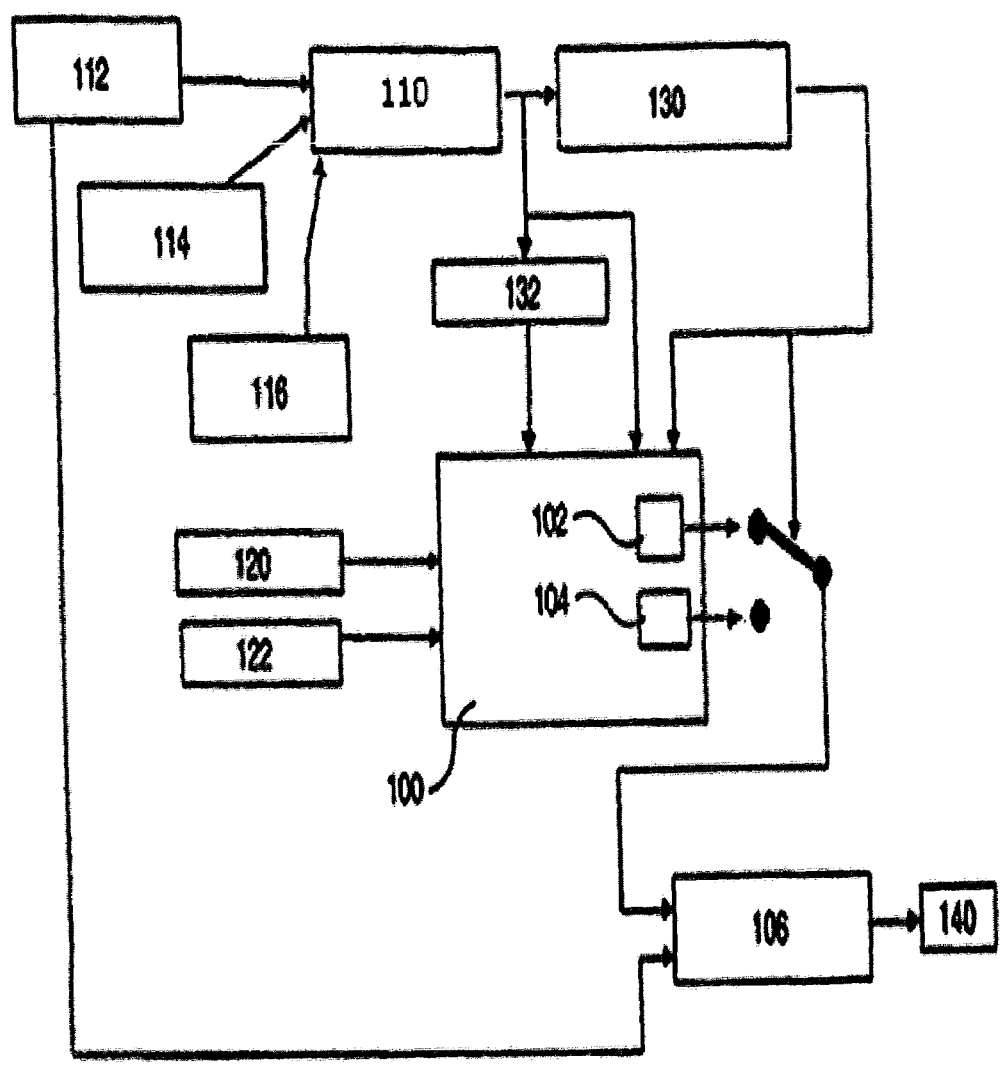
FIG. 14 represents the way the tension to apply to the stator is determinate.
Figure 15:
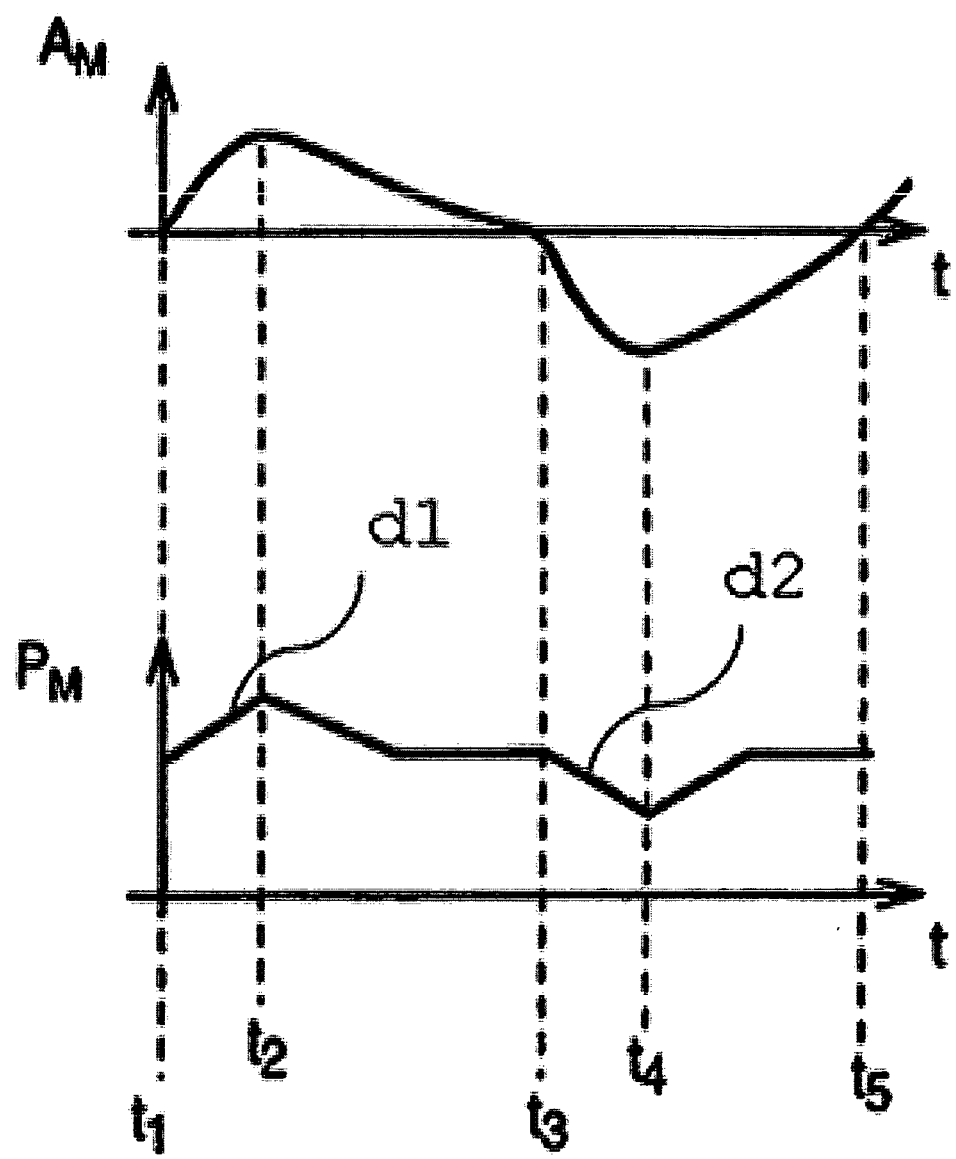
FIG. 15 represents an example of air pressure applied to the patient in respect of his respiration.
Figure 16A:
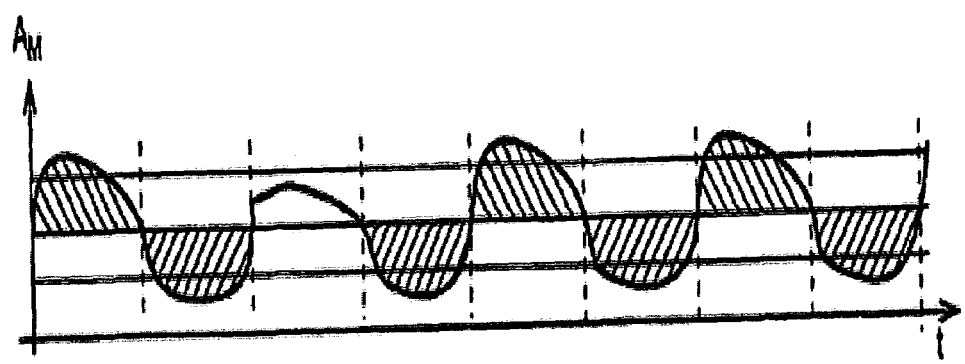
FIGS. 16a and 16b represent respectively the patient's 35 breathing pattern $A_M$ during time t and the pattern of the pressure of the air provided by the apparatus $P_M$ during time t according to present invention.
Figure 16B:

In a preferred embodiment of the present invention, the apparatus comprises means for measuring the patient's breathing parameters at the patients mask. These means are preferentially means that enables to determine the airflow. The apparatus allowing fast accelerations and decelerations allows to modulate the pressure to the patient in respect to the illness to treat. Based on the high speed and efficiency of the centrifugal blower, the apparatus can accommodate almost any kinds of pressure patterns to any kinds of breaths but only a few among those are useful in the respiratory treatments. The apparatus has thus the ability to differentiate the two basic states of the respiration: inspiration and expiration. Two of consecutive basic states constitute one breathing step. The sensors provided in the apparatus enables the pressure control unit 37 to determinate the pressure required for the patient and to send the corresponding Pulse Width Modulation PWM value to the micro controller 26. Preferentially the pressure control unit comprises an estimation module 100 or program which determine the pressure to apply, and comprises a control loop which converts this value of pressure into the tension PWM to apply to the blower. The determination by the pressure control 37 of the tension PWM to apply is represented in FIG. 14. The outputs of the estimation module 100 are the value of the inspiration pressure PI which is the pressure maintained at the patient's mask during the inspiration, and the value of the expiration pressure PE which is the pressure maintained at the patient's mask during the expiration. The patient's breathing parameters, and preferentially the airflow parameters, enables the computation of the inspiration and expiration, this latest computation enables the estimation module 100 to determinate, which step of the patient's breathing is occurring. A breath estimation module 132 is qualifying a breath in shape, energy(volume) and frequency. The clinician or a qualified user enters parameters or shapes of the delivered pressures for the expiration phase and the inspiration phase. The clinician entered also parameters 120 defining how the estimation module 100 is going to react following events detected in the breath estimation module. It is well known that a feedback of the patient with his treatment is helping compliance, thus the patient can have an access to a parameter 122 ranging from minimum to maximum that is qualified to be "comfort vs efficiency". This patient setting 122 is having the weight that the clinician is giving to it, from pure placebo effect to some level of effects. Basically the patient's settings are applied in the normal breath situation or/and have a limited action on the pressure regulation. It is also possible that the airflow is an input to the estimation module 100. Thus, with the data inputs concerning the breath estimation (and clinical symptoms or event associated with), the inspiration/expiration computation and the clinical settings, and possibly the airflow computation 110 and patient settings, the pressure control unit 37 by the estimation module 100 is able to determinate the pressures required PI and PE. Those two values can be addressed to two different outputs 102 and 104 where a switch is able, relative to the inspiration/expiration computation, to connect to the required output regarding if the patient is breathing in or out. The pressure control unit 37 comprises a pressure control loop 106 which, by comparing the pressure measured in the mask and the value of pressure required PI or PE, is able to adjust the tension PWM 140 in order to obtain the correct pressure in the mask. The FIG. 15 represents one pattern of the pressure of treatment provided according to the airflow due to the patient breathing. In this example, the clinical technician has set a special modulation of pressures PI and PE during respectively the inspiration and the expiration; after a while as no special event occurs the values of the two pressures are changed. The estimation module 100 can preferentially use a clock time 25 to time mark the breathing parameters.

The apparatus has a two steps, strong recognition, process in order to prevent false start of the apparatus when the mask is not on the patient's face and to prevent starting a new treatment session. When the apparatus is started by the patient by using the keyboard, for example and as represented in FIG. 13 by using the start key, the blower 33 is kept turning at a very low speed, waiting for some activity on the mask pressure sensors 23. When an activity is detected, the apparatus is instantaneously trying to bring the pressure at the apparatus outlet 9 at a minimum starting pressure $P_0$ of 4 hPa. This will guarantee that no $CO^2$ rebreathing will occur. When this pressure is reached the estimation module 100 tries to identify at least one breath to start the treatment process according to the settings. When the mask is not applied against something, like a hand or the patient's face, no activity is detected. Then if a maximum time has been spent (the timeout is reached) since the start key is actuated, without detecting any activity, the blower is stopped. On the contrary, the apparatus keeps on waiting for an activity on the pressure sensors. When the mask is not applied correctly the pressure can not reach 4 hPa. Then if the timeout is reached the blower is stopped, on the contrary the apparatus tries again to detect some activity on the pressure sensors. When the mask is not applied on the patient's face no breath pattern is recognized. Then the blower is stopped if the timeout is reached. On the contrary the estimation module 100 waits to detect some activity on the pressure sensors. The timeout checking prevents the blower keeping turning on if the patients does not start the treatment and forget to start the blower.

Preferentially, the data of the pressures PM 112 and PB 114 which are sensed at the extremities of the tube and the data 116 of the tube coefficient $K_T$ enable the airflow computation 130. One formula that can be use to compute the airflow from these values is:

$$\text{Airflow}^3 = (PM-PB)/K_T$$

The following examples demonstrate the way the estimation module 100 modulates the pressure value PM to apply to the patient's mask.

EXAMPLE 1

Pressure Pm at Patient's Mask within a Breath

As represented in the FIG. 15 the pressure provided is not constant but is a function of time.

At time t1 the patient starts breathing in. Time t2 is defined when the absolute value of airflow starts to decrease within the inspiration phase or shows a fixed delay after t1. As the estimation module is calculating the derivative of the airflow function, it is able do determine this time for example when the derivative reaches zero. Time t3 is the start of expiration. Time t4 is defined when the absolute value of airflow starts to decrease within the expiration phase or shows a fixed delay after t3. Time t5 is the end of the breath step and the beginning of a next breath step.

In order to reduce the patient's lung effort the estimator increases the value of pressure PM from time t1 to t2. After time t2 as the absolute value of airflow is decreasing the estimation module decreases the pressure value. In the same way, to reduce the patient's lung effort the estimator decreases the value of pressure PM from time t3 to t4. After time t4 as the absolute value of airflow is decreasing, the estimation module increases the pressure value.

The value of PM given by the estimation module and thus the pressure applied at the mask is a function of time.

FIG. 15 represents one example of the PM function pattern on one breath step. This function is given by the following formula:

if $t1 < t \leq t2$: $P_M = P_T + (t-t1) \times S_{LH}$ if $t2 < t \leq t3$: $PM = \text{MAX}(P_T + (t2-t1) \times K_{RH} - (t-t2) \times SLH, AVP)$ wherein the MAX function returns the greatest of its two members, each member being separated in the parenthesis by a coma.

if $t3 < t \leq t4$: $PM = P_T + (t-t3) \times SLH$ if $t4 < t \leq t5$: $PM = \text{MIN}(AVP - (t4-t3) \times SLH + (t-t4) * SLH, AVP)$ wherein the MIN function returns the smallest of its two members, each member being separated in the parenthesis by a coma.

According to the FIG. 15 and these equations, the increases and decreases are linear, the absolute value of the slope coefficient $S_P$ being a constant set by the patient or the clinician. During one inspiration the pressure value Pm is always superior or equal to treatment pressure PT. In figure ? the pressure is constant just before t3 (as the first member of the MAX function is inferior to PT. During one inspiration the pressure value Pm is always inferior or equal to treatment pressure PT. On one breath step the mean of the average pressure value PM is equal to the treatment pressure PT.

Clinician could also define bounds wherein the estimation module would limit the SP value when SP is set by the patient.

This kind of operation is allowed with the apparatus according to the present invention, because it has the ability to precisely and quickly regulates the pressure.

EXAMPLE 2

Variations of the Average Pressure of Treatment as a Function Time According to Detected Events In a preferential embodiment the average pressure of treatment within one breath, that is to say within one breathing step, can be modulated according to the events occurring, such as snoring or apneas or abnormal breathing patterns.

The apparatus will normally (no events detected)try to reduce the average pressure of treatment value, thus enhancing the patient comfort while breathing against the apparatus. The clinician set a minimum average pressure of treatment Ptmin and a coefficient NOEK expressed in hPa/s.

In the following example the terms AVP, are the average pressure of the pressure to patient's mask on one breath step. On FIG. 17, this average pressure as been noted PM, as the measurement is made on the first pressure sensor 6. As represented on FIG. 17, when no events are detected the average pressure of treatment value will follow the equation:

$$AVP(t) = \text{MAX}(AVP(t-\epsilon) - (NOEK \times \epsilon), AVP\text{min})$$

$\epsilon$ being the sampling time, which is the duration wherein the calculation is made, this sampling time corresponding to one breath step, the MAX function is returning the greatest value of its two members.

The average pressure value Pm thus decreases linearly until it reaches the minimum set by the clinician and stays constant until an event occurs.

When an event is detected, a 3 steps process is initiated

Step 1: the estimation module, looking in the clinical settings is defining if the event has to affect the average value of pressure PT.

Step 2: If so the estimation module looking in clinical settings, will define a persistence delay $D_P$.

Figure 17:
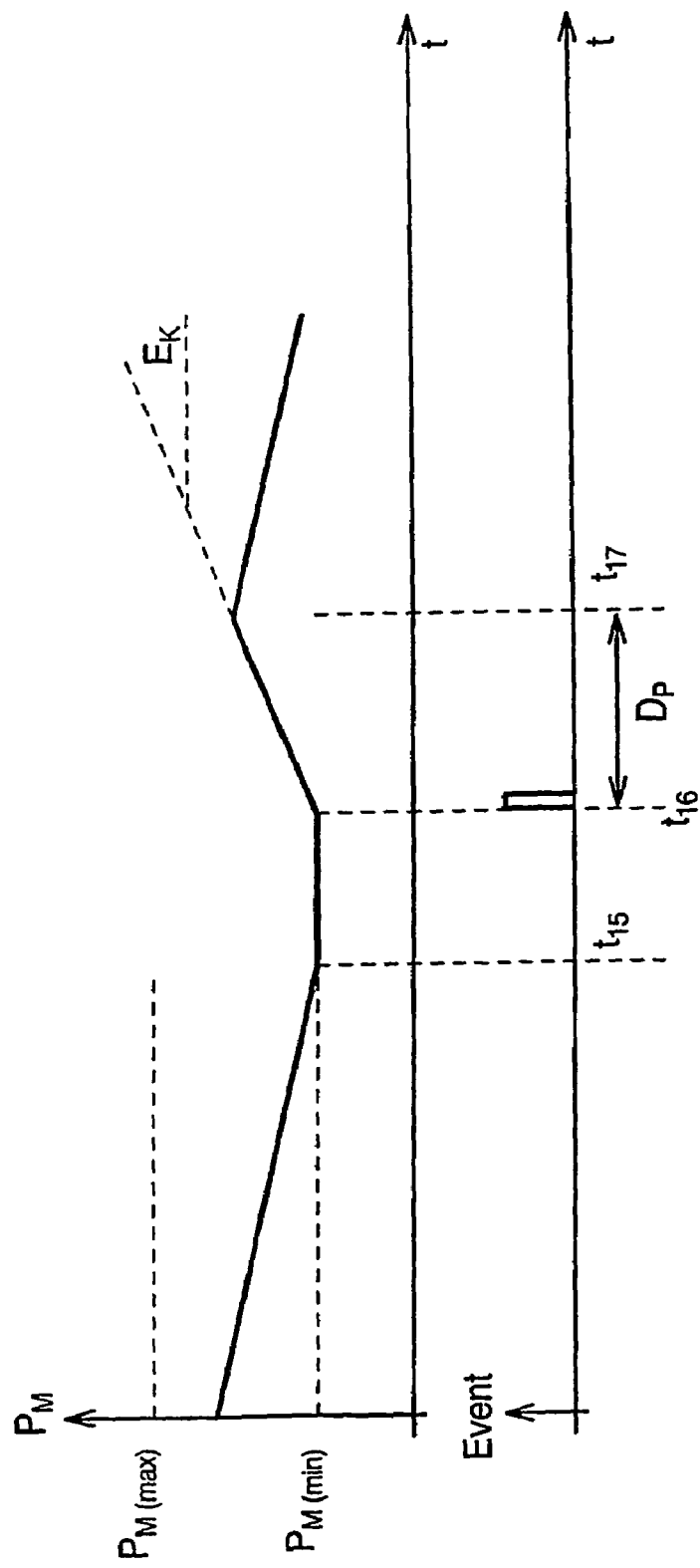
FIG. 17 represents one way the apparatus reacts to an event.

In the example of FIG. 17 a snore is detected, the persistence delay could be set to 2 minutes.

Step 3: A Ek parameter in hPa/s is extracted from clinical settings and balanced with an eventual ongoing event. The estimation module will determine the Ek corresponding to the event which occurs or has occurred and linearly increase the average pressure of treatment with Ek as slope coefficient. AVP will then follow the equation:

$$AVP(t)=\text{MIN}(AVP(t-\epsilon)+(EK\times\epsilon),AVP\text{max})$$

$\epsilon$ being the sampling time, the MIN function is returning the smallest value of it's two members.

During the persistence delay even if no event occurs the estimation module will keep on increasing the average pressure of treatment PT.

EXAMPLE 3

Variations of the Slope SLH of the Value of Pressure PM Applied to the Patients Mask within a Breath The slope coefficient of the pressure applied function of time within a breath can also be modulated according to time. In a preferential mode this coefficient remains constant on each single breath step (one inspiration and one expiration), but can be changed from one step to another.

The apparatus will try to reduce the slope coefficient SP, thus enhancing the patient comfort while breathing against the apparatus. The clinician set a minimum the slope coefficient SP, and a coefficient $N_{SP}$ expressed in hPa/s.

The events are detected the slope coefficient SP value will follow the equation:

$$SLH(t)=\text{MAX}(SLH(t-\epsilon)-(NOES\times\epsilon),SLH\text{min})$$

$\epsilon$ being the sampling time, the MAX function is returning the greatest value of its two members.

The shape of the corresponding curve is like the one for average pressure in FIG. 17.

When an event is detected, a 3 steps process is initiated:

Step 1: the apparatus, looking in the clinical settings is defining if the event has to affect SP Step 2: If so the apparatus looking in clinical settings, will define a persistence delay further named DS.

If, as represented on FIG. 18 a snore is detected, the persistence delay could be set to 2 minutes.

Step 3: A ES parameter in hPa/s$^2$ is extracted from clinical settings and balanced with an eventual ongoing event. The estimation module will determine the Ek corresponding to the event which occurs or has occurred and linearly increase the average pressure of treatment with ES as slope coefficient. SP will then follow the equation:

$$SLH(t)=\text{MIN}(SLH(t-\epsilon)+(ES\times\epsilon),SLH\text{max})$$

$\epsilon$ being the sampling time, wherein the calculation is performed, preferentially with a 200 Hz frequency the MIN function is returning the smallest value of it's two members.

During the persistence delay even if no event occurs the estimation module will keep on increasing the slope SP.

EXAMPLE 4 d1, d2 Auto Adjustment

On the FIG. 25 d1 and d2 have two different behaviors, according to t2 and t4 definitions. t2 is defined when the absolute value of airflow starts to decrease within the inspiration phase or shows a fixed delay after t1. t4 is defined when the absolute value of airflow starts to decrease within the expiration phase or shows a fixed delay after t3.

If t2 and t4 are defined according to the airflow waveform then no auto-adjustment is occurring. If not, following the same rules than SLH or AVP, the d1 and d2 can also be affected by the events. In the case when d1 and d2 are not locked by the breath waveform following the same process, d1 and d2 can also be adjusted according to events in the case.

The invention claimed is:

1. An apparatus to assist a patient's respiration by delivering air to the patient through a mask, comprising an air blower wherein an impeller is rotated by an electromotor comprising a rotor and a stator, said stator having at least three sectors, the rotation of the rotor being enabled by changes of the polarity of the sectors, each sector's polarity configuration constituting one step of the rotor's rotation, said apparatus further comprising a driving unit controlling changes of the sectors' polarity configuration such that the electromotor enables the blower to achieve fast accelerations and decelerations within one patient's breath step, said breath step consisting of one inspiration and one expiration; wherein said driving unit comprises means to sense a back electromotor force generated by the electromotor for changing the sectors' polarity configuration when the back electromotor force reaches a zero value.

2. The apparatus according to claim 1, wherein said stator has at least three sectors, each of said sectors being connected to one switch connected to a positive plot of a power supply and each of said sectors being connected to one switch connected to a negative plot of the power supply, in order that one of the rotor's rotation step is obtained when said driving unit applies tension to the stator by connecting the first sector to said positive plot, connecting the second sector to the negative plot and setting the third sector not connected to a power supply plot, thus enabling to measure the back electromotor force of the motor between the third sector and the negative plot, said driving unit changing the sectors polarity configuration when the back electromotor force reaches a zero value.

3. The apparatus according to claim 2, wherein said tension applied is a Pulse Width Modulation, the driving unit connecting one of said stator sectors to the positive plot during a first duration of time and then, during a second period, disconnecting the same sector from the positive plot and connecting it to the negative plot, so that in case of deceleration of the motor the generated current is sent to the negative plot, thus providing a fast deceleration of the impeller.

4. The apparatus according to claim 2, wherein said stator is a three sectors stator and said rotor is a dipole magnet, said stator thus having six sectors polarity configuration so that the rotor performs one 360 degree rotation in six rotation steps.

5. The apparatus according to claim 1, wherein said stator is a toroidal stator and wherein each of said sectors are coils each connected with a respective wire to each other.

6. The apparatus according to claim 5, wherein said stator is obtained by a strip wound cores technique with a high grade thin silicon steel, of about 0.05 mm thickness.

7. The apparatus according to claim 1, wherein when the blower is functioning and no back electromotor force is measured, said driving unit fixes the tension applied and changes the sectors polarity configuration after a given time, said driving unit decreasing this given time every step until a back electromotor is detected and then applying the required tension and changing the sectors polarity configuration according to the back electromotor value.

8. The apparatus according to claim 1, further comprising bearings and a bearing holder, and wherein said impeller, said rotor and a shaft of said impeller are fixed together, an inner ring of the bearings being fixed to said shaft and outer rings of said bearings being held by the bearing holder, which is fixed in the apparatus, and said rotor being shifted outside the stator, so that the stator also generates on the rotor an axial force oriented along said shaft, thus generating a preload on the bearings.

9. The apparatus according to claim 8, wherein said rotor is shifted outside of the stator at an equal distance of each of the at least three stator sectors.

10. The apparatus according to claim 1, further comprising a power supply manager adapted to be connected to a positive power supply source, said power supply manager comprising a current sensor, a comparator, a load resistor and a means to switch on the load resistor between the positive power supply and a ground when the current measured by said current sensor is negative, in order to dissipate this current in said load resistor by thermal effect.

11. The apparatus according to claim 1, being designed to be connected to a tube having a diameter less than 22 millimeters, a first extremity of the tube being connected to an air outlet of the blower and a second extremity of the tube being connected to a mask in which the patient breaths.

12. The apparatus according to claim 1, further comprising: at least one means for detecting the patient's breathing parameters, a pressure control unit to adjust a pressure delivered by said blower at the level of said mask, and comprising an estimation module connected to the means for detecting the patient's breathing parameters, in order that the estimation module is able to determine when the patient is inspiring or expiring and in response the pressure to apply to the patient's mask, during inspiration and during expiration.

13. The apparatus according to claim 12, wherein said at least one means detects the patient's airflow and sends it to a breath estimator which determines the airflow as a function of time and transmits this function to said estimation module which will thus estimate the pressure to apply to patient's mask according to the airflow function, in order to decrease the effort of the patient's lung while maintaining, during one breath step, the average value of the pressure at the mask ($P_M$) equal to the pressure of treatment.

14. The apparatus according to claim 13, wherein said estimation module determines the pressure ($P_M$) at the mask as a function of time.

15. The apparatus according to claim 12, wherein the control unit comprises a nonvolatile memory in which a clinician can enter clinical settings comprising at least the treatment pressure and optionally the pressure to apply according to the patient's breathing parameters, said estimation module providing the pressure at the mask ($P_M$) according to these clinical settings and to the patient's breathing parameters.

16. The apparatus according to claim 15, wherein the patient can enter patient settings in said nonvolatile memory, said estimation module providing the pressure at the mask according to these patient settings and to the patient's breathing parameters within bounds given by the clinician settings.

17. The apparatus according to claim 12, in which the estimation module is able to determine that an event occurs in patient's breathing thus enabling said pressure control unit to provide the blower with the tension to apply to adjust the pressure at patient's mask.

18. The apparatus according to claim 12, wherein said means for detecting the patient's breathing parameters enable the pressure control unit to compute the airflow at patients mask, said estimation module determining that an event is occurring with the airflow parameters or shape.

19. The apparatus according to claim 12, wherein said estimation module has an inspiration output where said estimation module sets the mask pressure (PM) value during inspiration, and wherein said estimation module has an expiration output where said estimation module set the mask pressure (PM) value during expiration, said pressure control unit comprising a switch which is connected alternatively to the inspiration output or expiration output according to the patient's breathing.

20. The apparatus according to claim 12, wherein the means for detecting the patient's breathing parameters comprises a pressure sensor for sensing the pressure at a first tube extremity and one pressure sensor for sensing the pressure at an extremity of the tube connected to the blower outlet, an airflow computation module being able to calculate the airflow from these pressures and from an tube airflow resistance coefficient (KT).

21. The apparatus according to claim 12, wherein the apparatus further comprises a starting means which, when actuated, orders the estimation module to detect a breathing activity, said estimator module sending an instruction to stop the blower if no activity is sensed after a given delay.

22. The apparatus according to claim 1, wherein a power supply manager comprises a communication module which transmits data through the power source wires.

23. The apparatus according to claim 22, wherein said communication module comprises:
   a Frequency Shift Keying (FSK) modulator which transforms binary data sent by apparatus sensors or elements in a modulation of a frequency of the tension applied on a voltage controlled current source, connected to the external power supply so that the voltage controlled current source transmits the modulation corresponding to the data, and
   a FSK demodulator converting the voltage frequency modulation into binary data and transmits it to the elements, so that each sensor or module connected to the power source is able to receive or transmit information.

24. The apparatus according to claim 1, further comprising a phonic insulation box wherein the blower is placed, said impeller having a size less than 60 mm and comprising between 15 and 45 blades, so that the impeller rotates at a speed that generates a sound at a high frequency, enabling said box to insulate the patient from noise.

25. The apparatus according to claim 24, wherein said impeller has 27 blades.

26. The apparatus according to claim 1, wherein said apparatus is adapted to be used for the treatment of a breathing anomaly.

27. The apparatus according to claim 26, wherein said breathing anomaly is selected from the group consisting of snoring, apnea or hypoapnea.

* * * * *